(12) United States Patent
Nam et al.

(10) Patent No.: US 8,006,541 B2
(45) Date of Patent: Aug. 30, 2011

(54) DEVICE FOR DETECTING MICRO PARTICLES IN GAS AND A METHOD FOR FABRICATING THE DEVICE

(75) Inventors: Yun Woo Nam, Yongin-si (KR); Hyo-Il Jung, Seoul (KR); Seung Jae Lee, Seoul (KR); Hui-Sung Moon, Seoul (KR)

(73) Assignees: Samsung Electronics Co., Ltd., Suwon-si (KR); Industry-Academic Cooperation Foundation, Yonsei University, Seoul (KR)

( * ) Notice: Subject to any disclaimer, the term of this patent is extended or adjusted under 35 U.S.C. 154(b) by 608 days.

(21) Appl. No.: 12/145,590

(22) Filed: Jun. 25, 2008

(65) Prior Publication Data

US 2009/0282899 A1    Nov. 19, 2009

(30) Foreign Application Priority Data

May 13, 2008    (KR) .................. 10-2008-0044107

(51) Int. Cl.
*G01N 1/00* (2006.01)
(52) U.S. Cl. .................................... 73/28.04
(58) Field of Classification Search ............. 73/28.01, 73/28.04
See application file for complete search history.

(56) References Cited

U.S. PATENT DOCUMENTS

| 4,282,016 | A | * | 8/1981 | Tauber et al. | .................. 96/212 |
| 4,336,329 | A |   | 6/1982 | Hesse et al. | |
| 5,092,156 | A | * | 3/1992 | Miskolczy | ................ 73/863.12 |
| 5,249,462 | A | * | 10/1993 | Bonne | ........................ 73/204.21 |
| 5,493,890 | A | * | 2/1996 | Dussault et al. | ............... 73/1.06 |
| 6,019,817 | A |   | 2/2000 | Seagle | |
| 6,082,185 | A | * | 7/2000 | Saaski | .......................... 73/64.56 |
| 7,631,567 | B1 | * | 12/2009 | Hill | ............................. 73/863.22 |
| 7,678,256 | B2 | * | 3/2010 | Davalos et al. | ............... 204/547 |

FOREIGN PATENT DOCUMENTS

WO        79/01074        12/1979

* cited by examiner

*Primary Examiner* — John Fitzgerald
(74) *Attorney, Agent, or Firm* — Sughrue Mion, PLLC (57) ABSTRACT

A device for detecting micro particles in gas, which comprises: an inlet through which a gaseous sample including micro particles flows in; an outlet through which the sample flows out; a channel through which the sample flows from the inlet toward the outlet; a cooling layer which cools and condenses the sample flowing in the channel; a reservoir which is positioned on the cooling layer and collects the condensed sample; a detector which is positioned in the reservoir on the cooling layer and detects the micro particles included in the collected sample; and a heater which heats the outlet portion to produce a pressure difference between the inlet portion and the outlet portion, so that the sample flows through the channel from the inlet toward the outlet. The device for detecting micro particles in gas provides the advantage that micro particles included in gaseous sample can be detected without having to use additional pump or collector, detection time can be reduced, and detection accuracy can be improved.

6 Claims, 6 Drawing Sheets

DEVICE FOR DETECTING MICRO PARTICLES IN GAS AND A METHOD FOR FABRICATING THE DEVICE

PRIORITY STATEMENT

This application claims priority to Korean Patent Application No. 10-2008-44107 filed on May 13, 2008, under 35 U.S.C. §119, the contents of which in their entirety are incorporated herein by reference.

BACKGROUND

1. Field

The present invention relates to a device for detecting micro particles in gas and a method for fabricating the device, more particularly, to a device for detecting specific micro particles such as microorganisms included in gaseous sample using a micro convection pump, a cooling element and a dielectrophoretic impedance (DEPIM) sensor, and a method for fabricating the device.

2. Discussion of Related Art

With the recent rapid industrialization, pollution is becoming a serious problem. The bioenvironmental industry for diagnosing contamination by pathogenic or harmful microorganisms will become more and more important. In particular, the technique of detecting microorganisms floating in the air is of great importance. The technique is applied in such appliances as air conditioner, air cleaner, air controller, and the like, and may find use against bioweapon using microorganisms.

As the techniques of detecting the concentration of microorganisms included in a particular sample, there are an optical method of detecting fluorescence of particular wavelength emitted when the molecules constituting a microorganism are irradiated with light of specific wavelength; a molecular analytical method of detecting the presence of DNA, RNA or protein or changes thereof such as PCR, ELISA, or the like; an electrical method of detecting change of electrical signals as a microorganism passes through between electrodes; and so forth.

The above information disclosed in this Background section is only for enhancement of understanding of the background of the invention and therefore it may contain information that does not form the prior art that is already known in this country to a person of ordinary skill in the art.

SUMMARY

To attain the aforesaid objects, the present invention provides device for detecting micro particles included in gaseous sample and a method for fabricating the device.

In an aspect, the present invention provides a device for detecting micro particles in gas, which comprises: an inlet through which a gaseous sample including micro particles flows in; an outlet through which the sample flows out; a channel through which the sample flows from the inlet toward the outlet; a cooling layer which cools and condenses the sample flowing in the channel; a reservoir which is positioned on the cooling layer and collects the condensed sample; a detector which is positioned in the reservoir on the cooling layer and detects the micro particles included in the collected sample; and a heater which heats the outlet portion to produce a pressure difference between the inlet portion and the outlet portion, so that the sample flows through the channel from the inlet toward the outlet.

In another aspect, the present invention provides a method for fabricating a device for detecting micro particles in gas, which comprises the steps of: forming a cooling layer which cools and condenses a gaseous sample including micro particles, on a first substrate; forming an insulating film which provides an electrical insulation, on the cooling layer; forming a detector which detects the micro particles included in the sample, on the cooling layer; forming a heater which produces a pressure difference between an inlet portion and an outlet portion by heating, on the first substrate; forming a channel through which the sample flows by the pressure difference produced by the heater, between a second substrate and the first substrate; forming an inlet through which the sample flows in and an outlet through which the sample flows out by etching the second substrate; and covering the first substrate with the second substrate and bonding the first substrate and the second substrate to each other.

In a preferred embodiment of the present invention, the channel is formed by the steps of: forming a first channel layer which is formed on the first substrate, exposes the heater and the detector, and comprises a reservoir which is positioned on the cooling layer and collects the condensed sample; and forming a second channel layer which is formed on the second substrate and exposes part of the second substrate.

BRIEF DESCRIPTION OF THE DRAWINGS

The above and other objects, features and other advantages of the present invention will be more clearly understood from the following detailed description taken in conjunction with the accompanying drawings, in which.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations and shapes will be determined in part by the particular intended application and use environment.

In the figures, the same reference numerals refer to the same or equivalent parts.

DETAILED DESCRIPTION OF EXAMPLE EMBODIMENTS

Hereinafter, reference will be made in detail to various embodiments of the present invention, examples of which are illustrated in the accompanying drawings and described below. While the invention will be described in conjunction with exemplary embodiments, it will be understood that the present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

Figure 1:
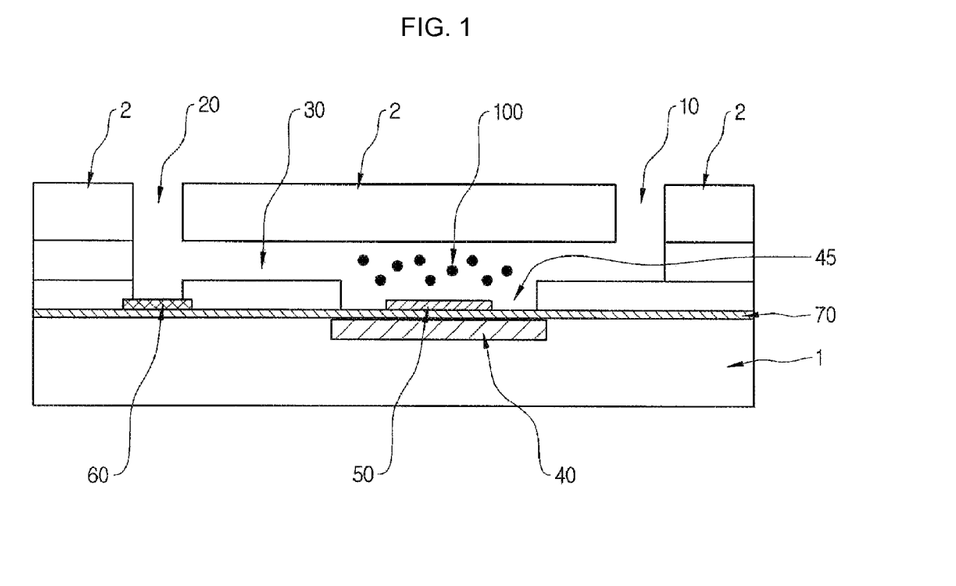
FIG. 1 is a transverse cross-sectional view schematically illustrating an example embodiment of a device for detecting micro particles in gas according to the present invention.

FIG. 1 is a transverse cross-sectional view schematically illustrating an example embodiment of a device for detecting micro particles in gas according to an embodiment of the present invention. Referring to FIG. 1, the embodiment of a device for detecting micro particles in gas according to the present invention comprises an inlet 10 through which a gaseous sample including micro particles 100 flows in, an outlet 20 through which the sample flows out, a channel 30 through which the sample flows between the inlet 10 and the outlet 20, a cooling layer 40 which cools and condenses the sample flowing through the channel 30, a reservoir 45 which collects the condensed sample, a detector 50 which detects the micro particles included in the collected sample, and a heater 60 which generates the flow of the sample in the channel 30.

The channel 30 is formed using substrates 1, 2 made of oxide, nitride or polymer material. Through the inlet 10, the sample including the micro particles 100 flows in. The sample flows through the channel 30 toward the outlet 20. The sample is a material suitable to carry the micro particles 100 and may be gas, such as air. The width, length and depth of the channel 30 may be determined appropriately considering the flow volume of the sample.

The cooling layer 40, the reservoir 45, the heater 60 and the detector 50 are positioned at the lower portion of the channel 30 between the inlet 10 and the outlet 20. The cooling layer 40 cools and condensed the sample so that it can be collected. In an embodiment of the present invention, the cooling layer 40 layer may comprise a Peltier element which utilizes the Peltier effect by which heat is absorbed at the interface between two different metals when a current flows. Between the cooling layer 40 and the lower portion of the channel 30, an insulating film 70 is positioned to provide electrical insulation.

The sample flowing in the channel 30 cools down and condenses when passing above the cooling layer 40, and is collected in the reservoir 45 positioned above the cooling layer 40. For example, an air sample passing above the cooling layer 40 may be condensed by the cooling layer 40, and collected in the reservoir 45 positioned above the cooling layer 40. Part of the sample condensed by the cooling layer 40 and collected in the reservoir 45 is present on the detector 50 located in the reservoir 45. The detector 50 detects the amount of the micro particles 100 included in the collected sample. For the detection of the micro particles, in an embodiment of the present invention, the detector 50 may comprise a dielectrophoretic impedance (DEPIM) sensor which detects the micro particles utilizing the dielectrophoresis (DEP) phenomenon.

The heater 60 is located at the lower portion of the channel 30 near the outlet 20. The heater 60 heats the outlet 20 portion and produces a pressure difference between the outlet 20 portion and the inlet 10 portion, thereby producing the flow of the sample in the channel 30. Due to the relatively low pressure at the outlet 20 portion, the sample flows through the channel 30 from the inlet 10 toward the outlet 20.

That is, by the heater 60, a convection pump linking the inlet 10, the channel 30 and the outlet 20 is formed. In such a construction, the sample is circulated by the heater 60 which is provided on the same substrate as the channel 30 and, therefore, an external pump for providing the sample into the channel 30 may be unnecessary.

After the detection of the micro particles has been completed as the sample passes through the cooling layer 40 and the detector 50, the sample is heated above the heater 60 and flows out through the outlet 20. Accordingly, in detection of micro particles such as microorganisms, thermal denaturation of the sample can be prevented and, thus, accurateness of detection of the micro particles can be improved.

Figure 2:
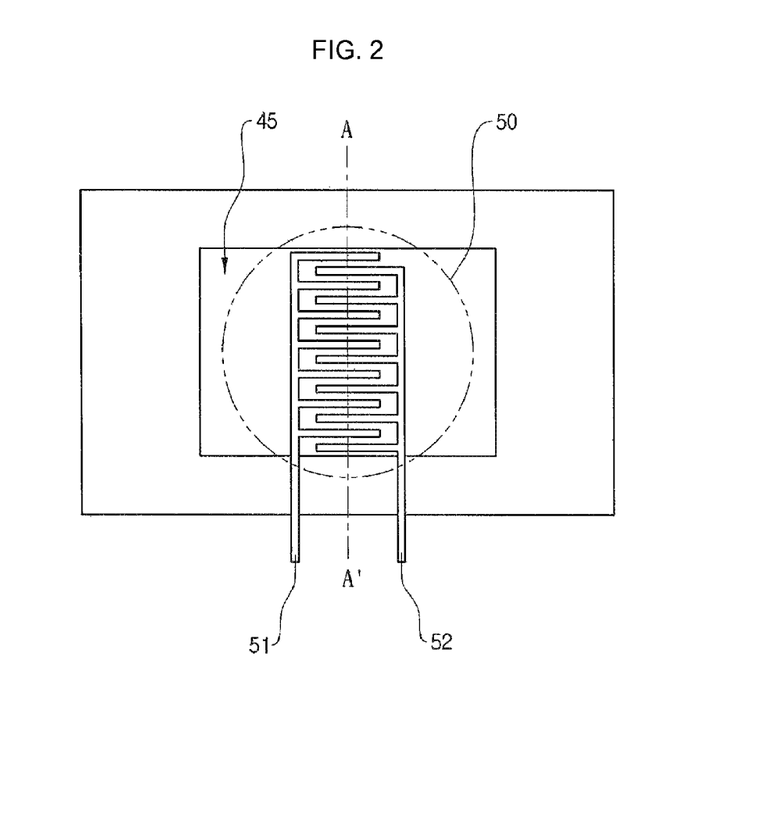
FIG. 2 is a partial, enlarged plan view illustrating the device for detecting micro particles in gas of FIG. 1.
Figure 3:
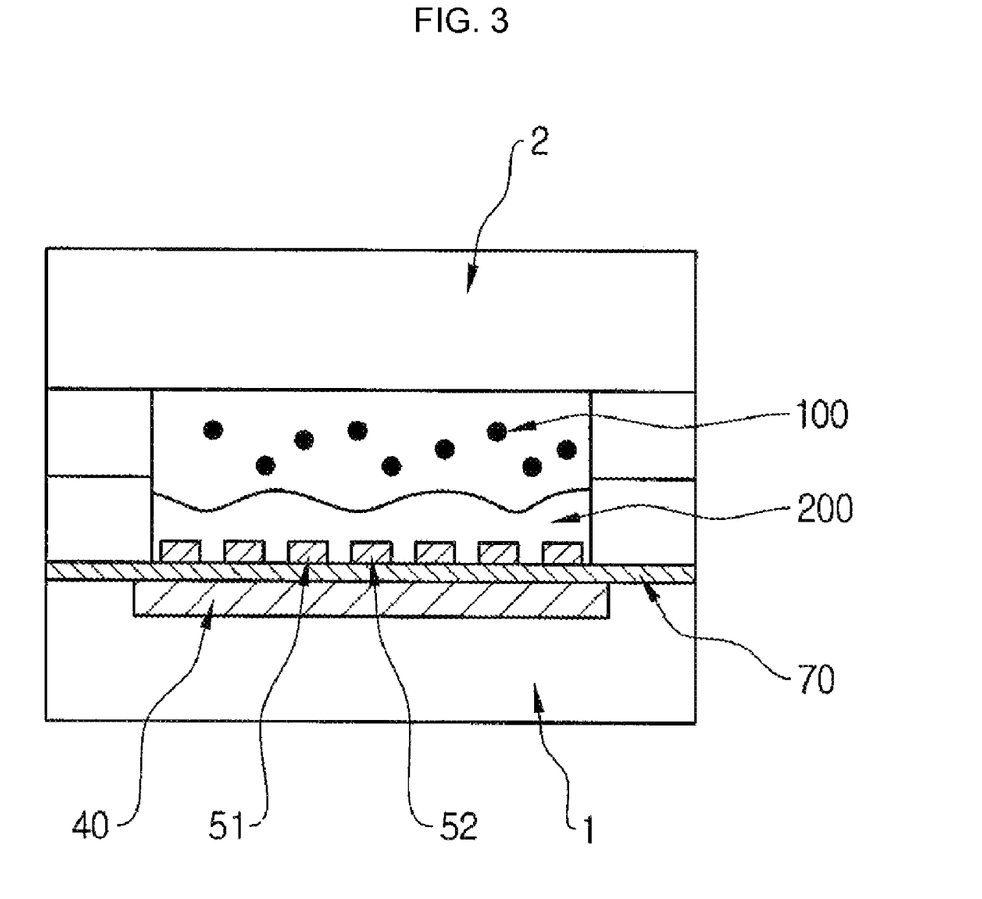
FIG. 3 is a longitudinal cross-sectional view illustrating the device for detecting micro particles in gas of FIG. 2 along line A-A'.

FIG. 2 is a partial, enlarged plan view illustrating the lower portion of the channel of the device for detecting micro particles in gas of FIG. 1, where the detector 50 is located. And, FIG. 3 is a longitudinal cross-sectional view illustrating the cross-section along line A-A' across the detector 50 shown in FIG. 2. The process of detecting micro particles by the detector 50 will be described referring to FIG. 2 and FIG. 3.

As described earlier, the sample flowing in the channel 30 is cooled and condensed as it passes above the cooling layer 40, and is collected in the reservoir 45. In the embodiment illustrated in FIG. 2, the detector 50 is composed of a pair of electrodes 51, 52 which are facing and spaced from each other. The pair of electrodes 51, 52 constitute a DEPIM sensor. In another embodiment, a DEPIM sensor may be composed of more than one electrode pairs.

The DEPIM sensor is a sensor which detects micro particles based on the change of impedance occurring between electrodes positioned in a solution in which the micro particles are dispersed, when the micro particles are collected at the electrodes by the DEP (dielectrophoresis) phenomenon as an alternating current (AC) electrical field is applied between the electrodes. In view of the DEP phenomenon, the micro particles included in the sample may be classified into (+) DEP particles, (−) DEP particles and (0 or zero) DEP particles. (+) DEP particles move toward the high-density electrical field direction, whereas (−) DEP particles move toward the low-density electrical field direction. Meanwhile, (0 or zero) DEP particles are not affected by the electrical field.

The detector 50 comprises the pair of electrodes 51, 52, which is interdigitated electrode configuration. Between the two electrodes 51, 52, an AC power of a predetermined frequency is applied. For the application of the AC power, a contact (not illustrated) for the two electrodes 51, 52 is provided outside the substrate. As illustrated in FIG. 2, each of the electrodes 51, 52 is formed in bended shape, not in planar shape. Therefore, when a power is applied between the two electrodes 51, 52, a relatively high-density electrical field is formed at the bended portion of the electrodes.

Upon the application of electrical field, the sample 200 collected in the reservoir 45 positioned on the cooling layer 40 moves between the two electrodes 51, 52 by the DEP phenomenon. Depending on the DEP polarity, the micro particles 100 included in the sample move toward the high-density electrical field direction, toward the low-density electrical field direction, or without being affected by the electrical field. The movement of the micro particles 100 included in the collected sample 200 results in change of impedance between the two electrodes 51, 52. Based on the impedance change, the amount of the micro particles between the two electrodes 51, 52 can be detected.

In an embodiment of the present invention, by controlling the magnitude and frequency of applied electric field to above one pair of dielectrophoretic electrode, it is possible to carry out a qualitative analysis, including identity, dielectric constant, etc. of the collected micro particles.

Because the cooling layer 40 which collects the sample and the detector 50 which is a sensor detecting the micro particles are positioned close to each other, collection of the sample and detection of the micro particles can be carried out simultaneously, and the time required for the detection of micro particles can be reduced.

In another embodiment of the present invention, the construction of the electrodes of the detector 50 may be different from that of the pair of electrodes 51, 52 illustrated in FIG. 2. Because the DEPIM sensor detects micro particles based on the dielectrophoretic effect in a non-uniformly formed electrical field, the detector 50 may be constructed using any electrode structure capable of generating a non-uniform electrical field.

FIG. 4A through FIG. 4G illustrate an example embodiment of a process of fabricating a device for detecting micro particles in gas according to the present invention.

Figure 4A:
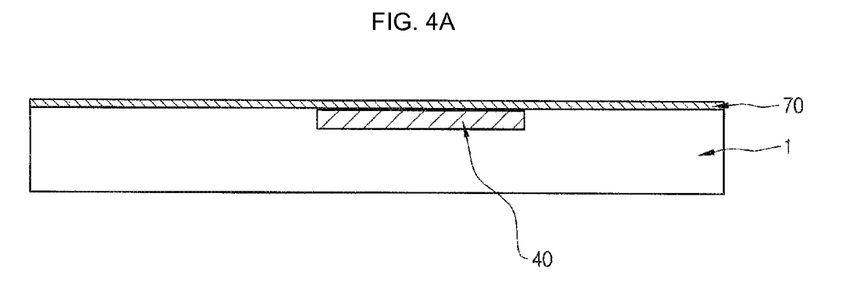
FIG. 4A through FIG. 4G are transverse cross-sectional views illustrating an example embodiment of a process of fabricating a device for detecting micro particles in gas according to the present invention.

First, as illustrated in FIG. 4A, a first substrate 1 comprising a silicon wafer is prepared. Then, a cooling layer 40 is formed on the first substrate 1. The cooling layer 40 may be formed on the first substrate 1 as a Peltier element using a semiconductor process. In another embodiment of the present invention, in case the first substrate 1 is made of glass or plastic material, the cooling layer 40 may be formed by attaching a Peltier element on the back side of the first substrate 1.

Then, as an insulating film 70 for providing an electrical insulation, an oxide film or a nitride film is deposited on the first substrate 1.

Figure 4B:
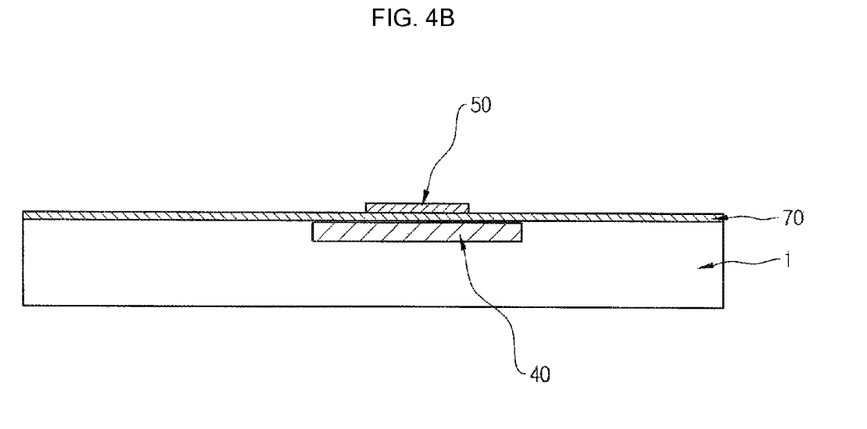

Next, as illustrated in FIG. 4B, a detector 50 is formed on the cooling layer 40. As described referring to FIGS. 1 through 3, the detector 50 is an element for detecting the micro particles utilizing the dielectrophoretic phenomenon, and may comprise one or more pair of electrodes. The detector 50 is formed by depositing a metal film made of aluminum (Al), copper (Cu), gold (Au), platinum (Pt), palladium (Pd), etc. followed by patterning the metal film through wet etching or dry etching, or Lift-off process of the metal film.

Figure 4C:
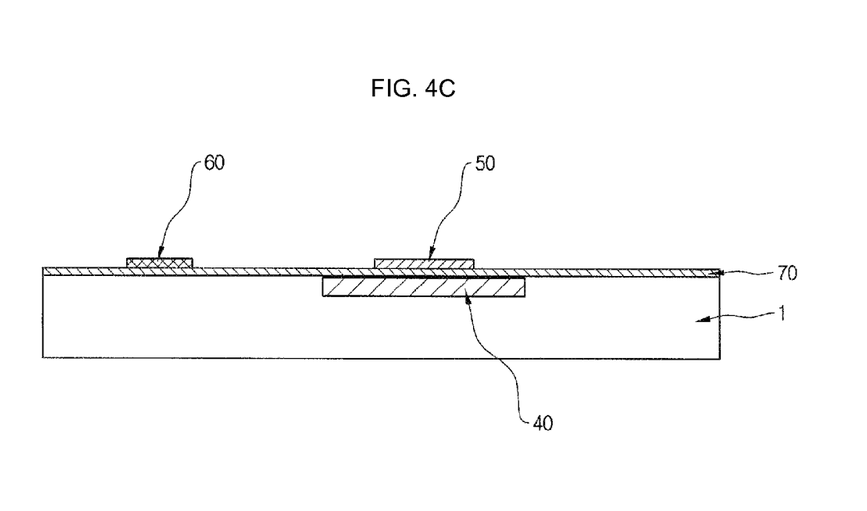

Next, as illustrated in FIG. 4C, a heater 60 is formed on the first substrate 1. The heater 60 is an element for producing a pressure difference between an outlet and an inlet by heating the outlet portion and, thereby, resulting in the flow of the gas sample through the channel. Accordingly, the heater 60 may be formed on the first substrate 1 at the portion where the outlet is to be formed. The heater may be formed by depositing a metal film made of aluminum (Al), copper (Cu), gold (Au), platinum (Pt), palladium (Pd), etc. followed by patterning the metal film through wet etching or dry etching, or Lift-off process of the metal film.

Figure 4D:
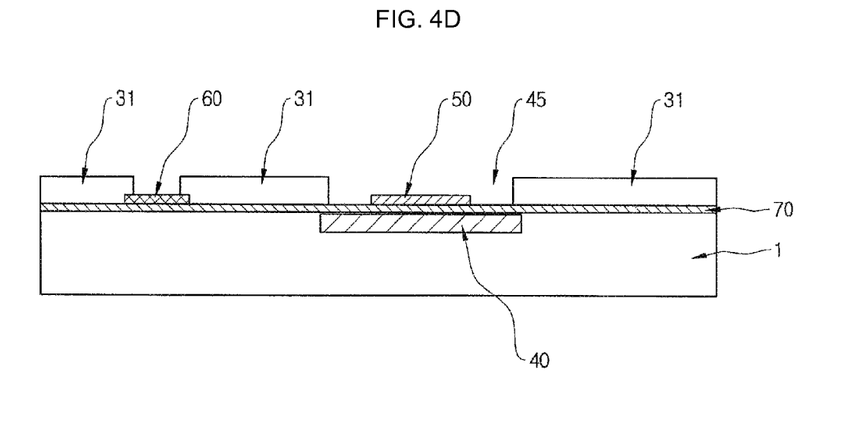

Then, as illustrated in FIG. 4D, a first channel layer 31 comprising a reservoir 45 in which the sample is condensed and collected is formed on the first substrate 1. The first channel layer 31 may be formed by depositing oxide film, nitride film or polymer film and patterning the deposited film. The patterning may be carried out such that the reservoir 45 is positioned above the cooling layer 40 and the heater 60 is exposed.

Figure 4E:
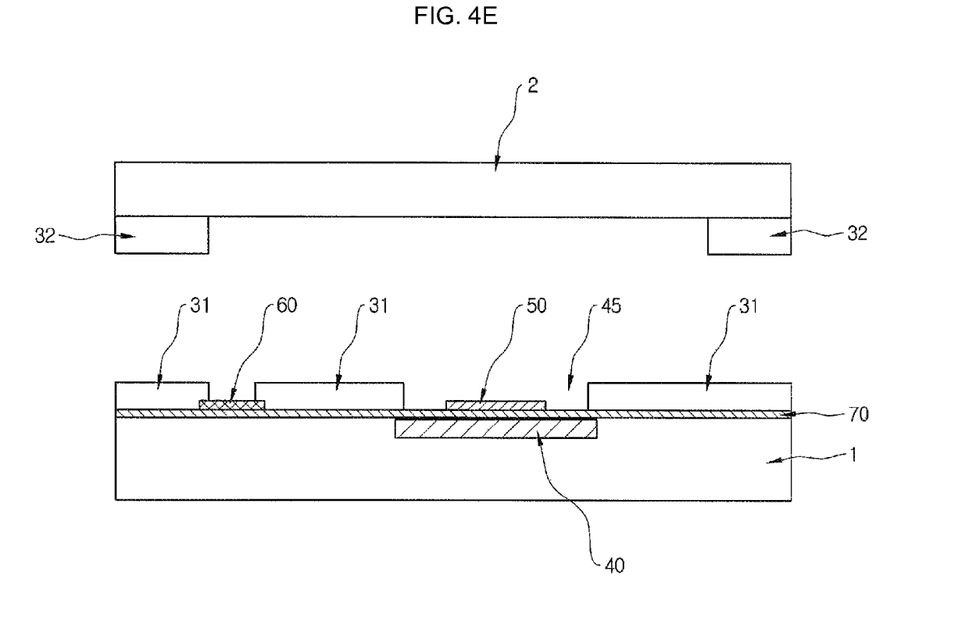

Then, as illustrated in FIG. 4E, a second channel layer 32 for forming a channel through which the sample flows is formed on a second substrate 2. The second channel layer 32 may be formed by depositing oxide film, nitride film or polymer film and patterning the deposited film. At this time, the portions where an inlet and an outlet will be located are exposed, and the first substrate 1 and the second substrate 2 are spaced by a predetermined thickness of the channel in order to provide a channel through which the sample flows.

Figure 4F:
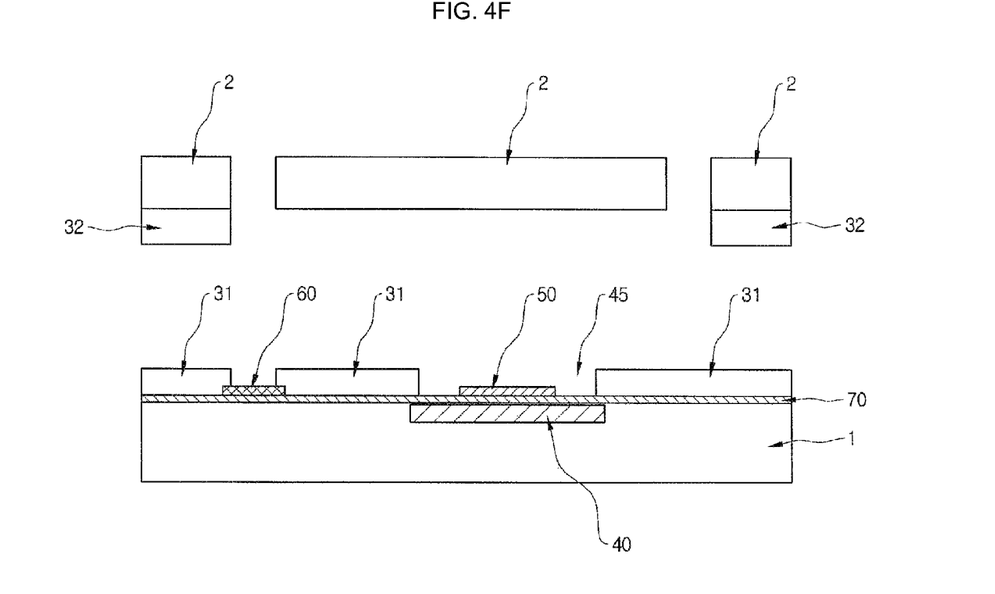

Next, as illustrated in FIG. 4F, a predetermined portion of the second substrate 2 is etched to form an inlet through which the sample flows into the channel and an outlet through which the sample flows out of the channel. As described referring to FIG. 4C, the outlet may be formed above the area where the heater 60 is located.

Figure 4G:
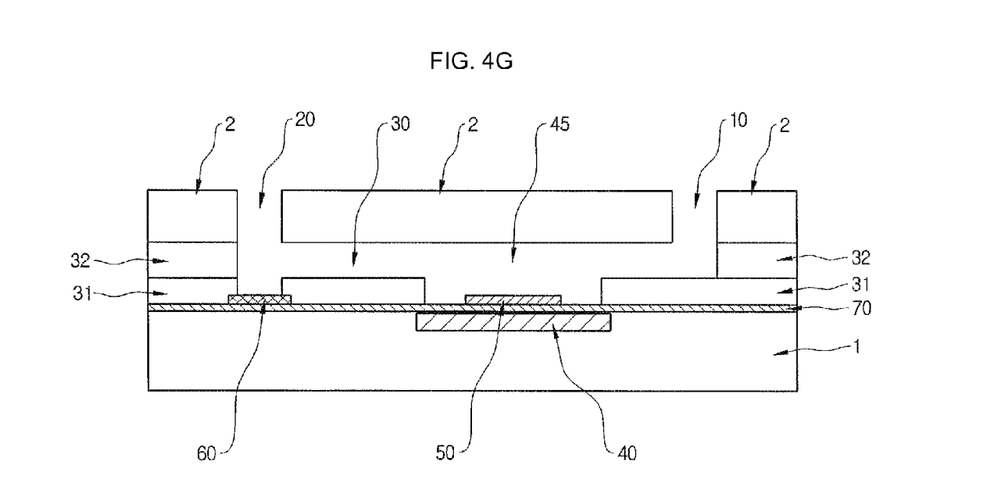

Finally, as illustrated in FIG. 4G, the first substrate 1 is covered by the second substrate 2 and the two substrates are bonded to each other. The first substrate 1 and the second substrate 2 are bonded to each other by bonding the first channel layer 31 and the second channel layer 32 to each other.

In the embodiment described above, the cooling layer 40, the detector 50 and the heater 60 are formed in separate process steps. However, in another embodiment of the present invention, more than one of the cooling layer 40, the detector 50 and the heater 60 may be formed in a single step, depending on the material constituting the elements.

Figure 5:
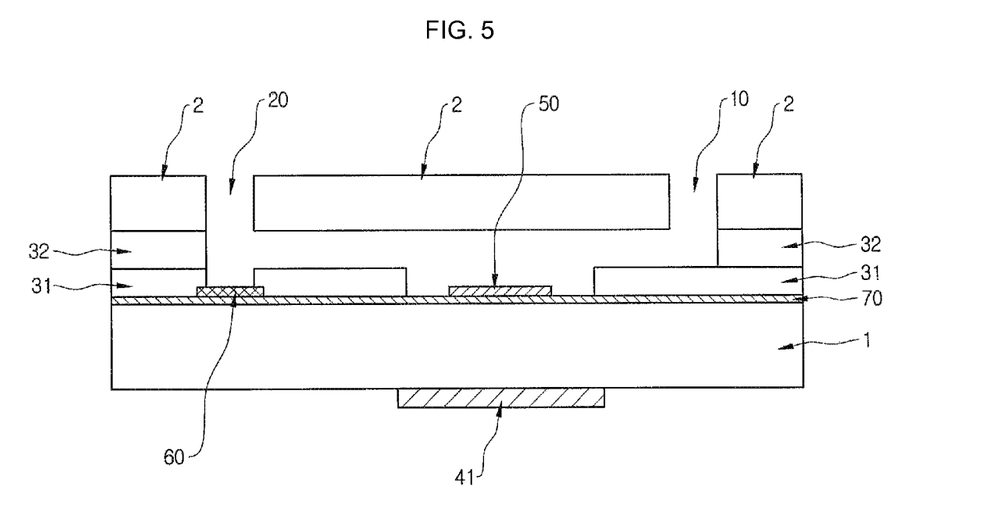
FIG. 5 is a transverse cross-sectional view schematically illustrating another example embodiment of a device for detecting micro particles in gas according to the present invention.

FIG. 5 is a transverse cross-sectional view schematically illustrating another example embodiment of a device for detecting micro particles in gas according to the present invention. Referring to FIG. 5, a cooling layer 41 is formed on the back side of the first substrate 1, not on the upper side.

In the embodiment described referring to FIG. 1 through FIG. 4, the cooling layer 40 is formed on the first substrate 1 and is directly connected to the channel 30. However, in the embodiment illustrated in FIG. 5, the cooling layer 41 is formed on the back side of the first substrate 1, and absorbs heat from the sample flowing in the channel, through the substrate 1. The sample flowing in the channel is cooled and condensed when it passes above the cooling layer 41, and is collected in the reservoir 45.

In the embodiment illustrated in FIG. 5, the cooling layer 41 is placed at the backside of the substrate 1. Therefore, in the fabricating process of the device for detecting micro particles in gas, the cooling layer 41 may be formed easily by attaching a proper element at the back side of the first substrate 1, without having to form the cooling layer 41 as integrated with the channel.

Although the preferred embodiments of the present invention have been disclosed for illustrative purposes, those skilled in the art will appreciate that various modifications, additions and substitutions are possible, without departing from the scope and spirit of the invention ad disclosed in the accompanying claims.

What is claimed is:

1. A device for detecting micro particles in a gas, which comprises:
   an inlet through which a gaseous sample including micro particles flows in;
   an outlet through which the sample flows out;
   a channel through which the sample flows from the inlet toward the outlet;
   a cooling layer which cools and condenses the sample flowing in the channel;
   a reservoir which is positioned on the cooling layer and collects the condensed sample;
   a detector which is positioned in the reservoir on the cooling layer and detects the micro particles included in the collected sample; and
   a heater which heats the outlet portion to produce a pressure difference between the inlet portion and the outlet portion, so that the sample flows through the channel from the inlet toward the outlet.

2. The device for detecting micro particles in gas as set forth in claim 1, wherein the channel comprises the cooling layer, the reservoir, the detector and the heater.

3. The device for detecting micro particles in gas as set forth in claim 1, wherein the detector comprises a dielectrophoretic impedance sensor consisting of one or more pair of electrodes which are facing and spaced from each other.

4. The device for detecting micro particles in gas as set forth in claim 1, wherein the cooling layer comprises a Peltier element.

5. The device for detecting micro particles in gas as set forth in claim 1, which comprises;
   a first substrate on which the cooling layer, the reservoir, the detector and the heater are formed; and
   a second substrate which is bonded on the first substrate, and on which the inlet and the outlet are formed.

6. The device for detecting micro particles in gas as set forth in claim 5, wherein the cooling layer is formed on the upper side or back side of the first substrate.

\* \* \* \* \*